US011918512B2

(12) United States Patent
Higgins et al.

(10) Patent No.: US 11,918,512 B2
(45) Date of Patent: Mar. 5, 2024

(54) OPHTHALMIC SPECIALTY INSTRUMENT FOR TREATING MEIBOMIAN GLAND DYSFUNCTION (MGD)

(71) Applicants: Donald J. Higgins, Plainville, CT (US); Stephanie Bealing, Plainville, CT (US); Tiffany McDaniel, Plainville, CT (US)

(72) Inventors: Donald J. Higgins, Plainville, CT (US); Stephanie Bealing, Plainville, CT (US); Tiffany McDaniel, Plainville, CT (US)

( * ) Notice: Subject to any disclaimer, the term of this patent is extended or adjusted under 35 U.S.C. 154(b) by 0 days.

(21) Appl. No.: 17/939,128

(22) Filed: Sep. 7, 2022

(65) Prior Publication Data
US 2023/0248567 A1 Aug. 10, 2023

Related U.S. Application Data

(60) Provisional application No. 63/307,406, filed on Feb. 7, 2022.

(51) Int. Cl.
*A61F 9/007* (2006.01)
*A61B 17/28* (2006.01)
(Continued)

(52) U.S. Cl.
CPC .......... *A61F 9/00772* (2013.01); *A61B 17/28* (2013.01); *A61B 17/30* (2013.01);
(Continued)

(58) Field of Classification Search
CPC .. A61F 9/007; A61F 9/00718; A61F 9/00772; A61B 17/29; A61B 17/30; A61B 17/28
See application file for complete search history.

(56) References Cited

U.S. PATENT DOCUMENTS 7,223,267 B2   5/2007  Isola et al.
10,376,273 B2  8/2019  Korb et al.
(Continued)

FOREIGN PATENT DOCUMENTS

CN   2035644408 U   11/2013
CN   105310817 B    9/2014
(Continued)

OTHER PUBLICATIONS

Scientific Labwares Stainless Steel Forceps with Offset Flat-Tips, https://www.amazon.com/Scientific-Labwares-Stainless-Forceps-Flat-Tips/dp/B07V3L125K/ref=sr_1_1_sspa?dchild=1&keywords=Scientific+Labwares+Stainless +Steel+Forceps+with+Offset+Flat-Tips&qid=1633359830&sr=8-1-spons&psc=1&smid=AEY16YDFF4GU2&spLa=ZW5jcnlwdGVkUXVhbGlmaWVyPUFZWIdUNk1KVkEyNjEmZW5jcnlwdGVKSWQ9QTA1MTY1MzUxTzdPSTBHRjZERFJPJmVuY3J5cHRlZEFkSWQ9QTAzMjAwMDUxN05LVEFVVKFUNVBHJndpZGd1dE5hbWU9c3BfYXRmJmFjdGlvbj1jbGlja1JlZGlyZWN0JmRvTm90TG9nQ2xpY2s9dHJ1ZQ&th=1.
(Continued)

*Primary Examiner* — Sarah W Aleman
(74) *Attorney, Agent, or Firm* — Bay State IP, LLC

(57) ABSTRACT

Certain aspects are directed to an ophthalmic specialty instrument configured to allow patients to treat MGD and other dry eye conditions themselves which is easy to operate and more effective. The ophthalmic specialty instrument comprises a main body of two arms with a distal end and a proximal end; wherein the two arms are pivotably coupled to a common connection point at the proximal end and a pair of angled and slightly wedged pressure plates are attached to the distal end of the two arms; wherein an exfoliating member is also attached to the proximal end; and wherein the pressure plates are angled downwardly and outwardly (Continued)

from the longitudinal planes of the arms and have gentle radius of curvature that match the curvature of eyelids to facilitate a substantially 90° approaching angle to the eyelid margin as opposed to making contact with the eyelids tangentially.

17 Claims, 9 Drawing Sheets

(51) Int. Cl.
  *A61B 17/30* (2006.01)
  *A61F 9/00* (2006.01)
(52) U.S. Cl.
  CPC ............... *A61F 9/00* (2013.01); *A61F 9/007* (2013.01); *A61F 9/00718* (2013.01); *A61F 9/00709* (2013.01)

(56) References Cited

U.S. PATENT DOCUMENTS

| | | | |
|---|---|---|---|
| 2017/0087009 A1* | 3/2017 | Badawi | A61K 8/0208 |
| 2020/0029950 A1* | 1/2020 | Sindt | A61F 9/00718 |
| 2020/0078211 A1* | 3/2020 | Badawi | A61F 7/02 |
| 2020/0188169 A1* | 6/2020 | McMahon | A61H 7/003 |
| 2020/0188171 A1* | 6/2020 | Minelli | A61F 7/007 |
| 2020/0345405 A1* | 11/2020 | Fishman | A61F 9/007 |

FOREIGN PATENT DOCUMENTS

| | | |
|---|---|---|
| CN | 205234758 U | 12/2015 |
| CN | 211272185 U | 11/2019 |

OTHER PUBLICATIONS

PVC Coated Bent Tip Tweezers, https://jetsinc.com/tools-and-equipments/tweezers/pvc-tweezers/pvc-coated-bent-tiptweezers/.
Scientific Labwares Stainless Steel General Purpose Lab Forceps with Curved Medium Point Tips,https://www.amazon.com/dp/B07V5ML63H/ref=sspa_dk_detail_0?psc=1&pd_rd_i=B07V5ML63H&pd_rd_w=UuAJI&pf_rd_p=887084a2-5c34-4113-a4f8-b7947847c308&pd_rd_wg=1aLa1&pf_rd_r=28KB5HCAA8XRN46NKZK3&pd_rd_r=8f39abeb-4558-418c-9766-ad07e27680e2&smid=AEY16YDFF4GU2&spLa=ZW5jcnlwdGVkUXVhbGImaWVyPUEyUFJMMUNOVIhNUkM4JmVuX3J5cHRlZElkPUEwNjg3NDElMjZYRjZLVEZYMElUUSZlbmNyeXB0ZWRZXB0ZWRZElkPUEwMzE5NTEzOFhZUjRNUjFNVVgzJndpZGdldE5hbWU9c3BfZGVOYWlsJmFjdGlvbj1jbGljaoJlZGlyZWN0JmRvTm90TG9nQ2xpY2s9dHJ1ZQ==#descriptionAndDetails.
Flat tip tweezers—Anti-Acid/Anti-Mag SS—serrated handles—tips: bent, thin, squared. OAL: 105mm-4.13", https://www.ideal-tek.com/scheda.php?m=search&f=8&c-general%20purpose%20tweezers&I=3&idp=716.
Barraquer Cilia Forceps, https://www.corzaeye.com/barraquer-cilia-forceps-k5-6000.
Barraquer Cilia Forceps, http://novosurgical.com/barraquer-cilia-forceps.html.
Bent End Tweezers, https://dollssoreal.com/products/hobby-stamp-eyelash-placement-tweezers.
Membrane Tweezers, https://us.misumi-ec.com/vona2/detail/223006649204/.

* cited by examiner

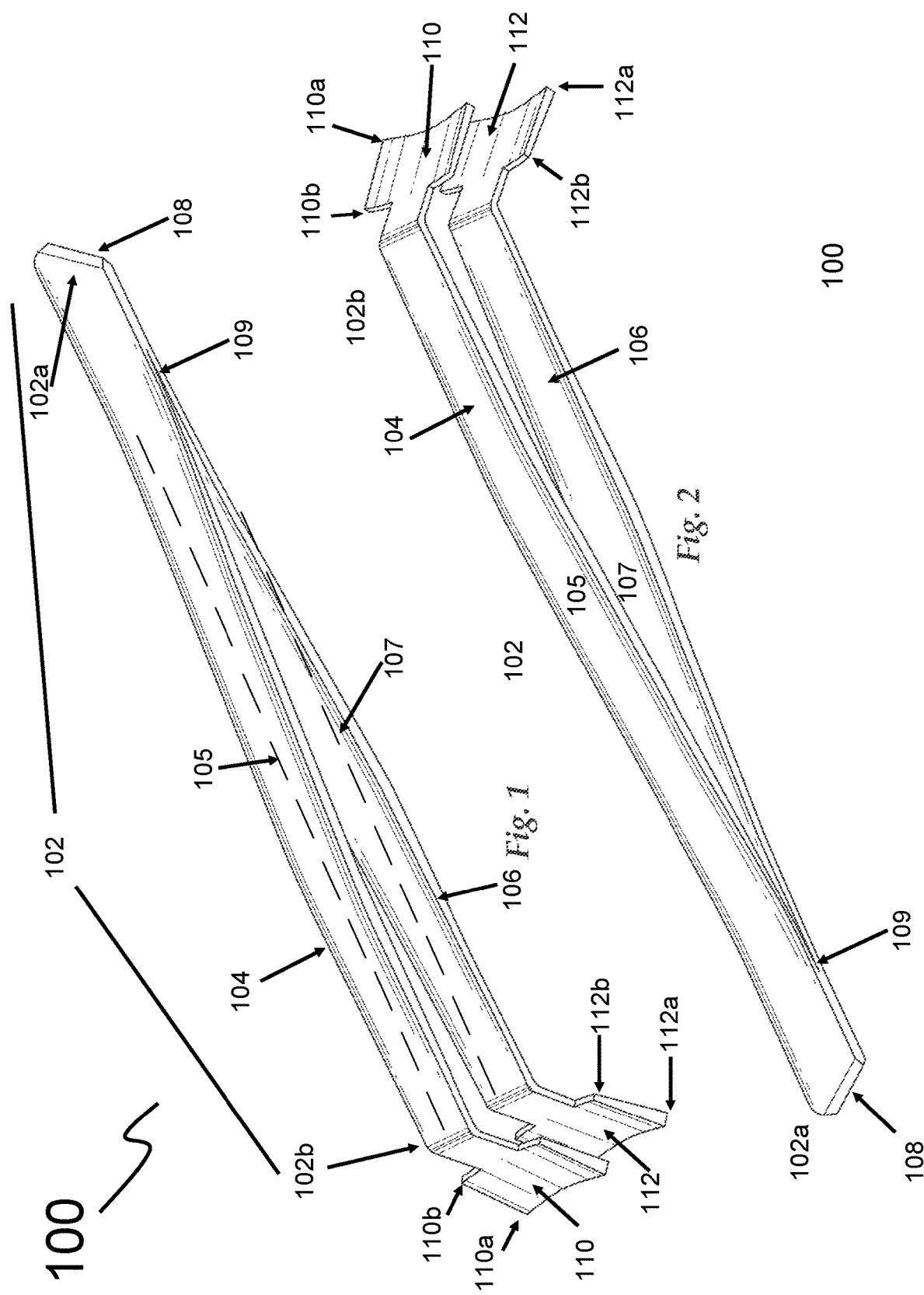

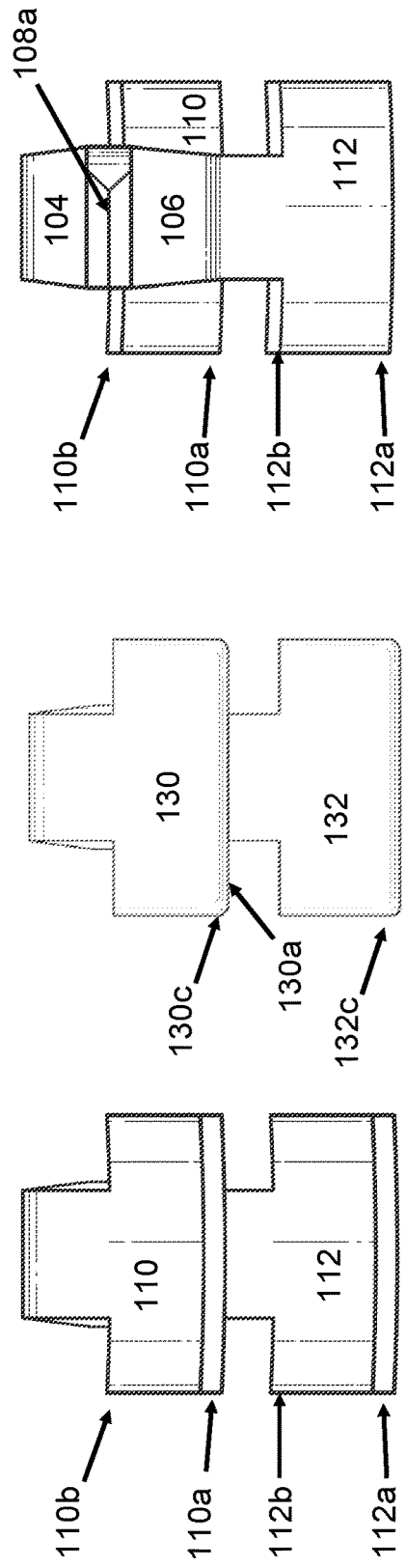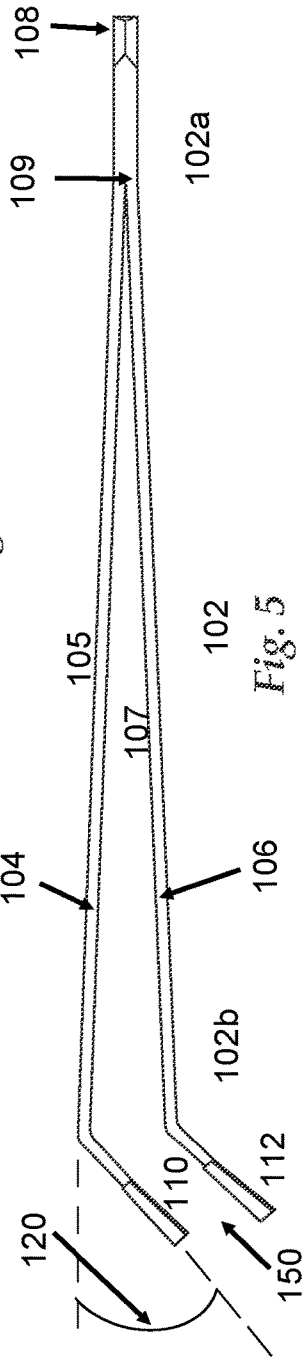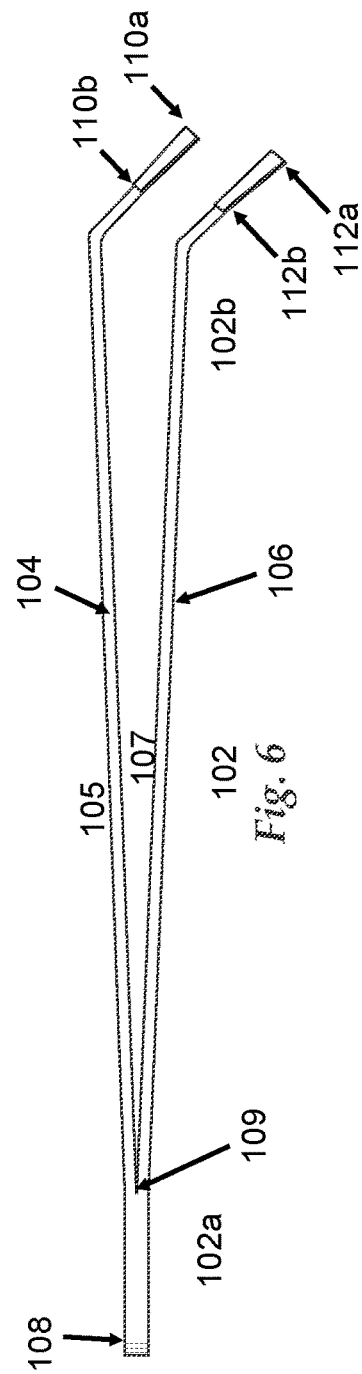

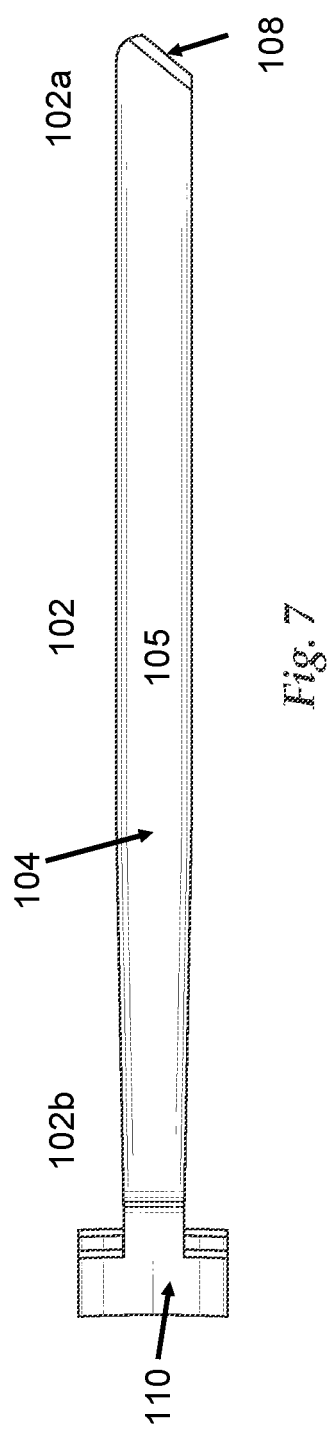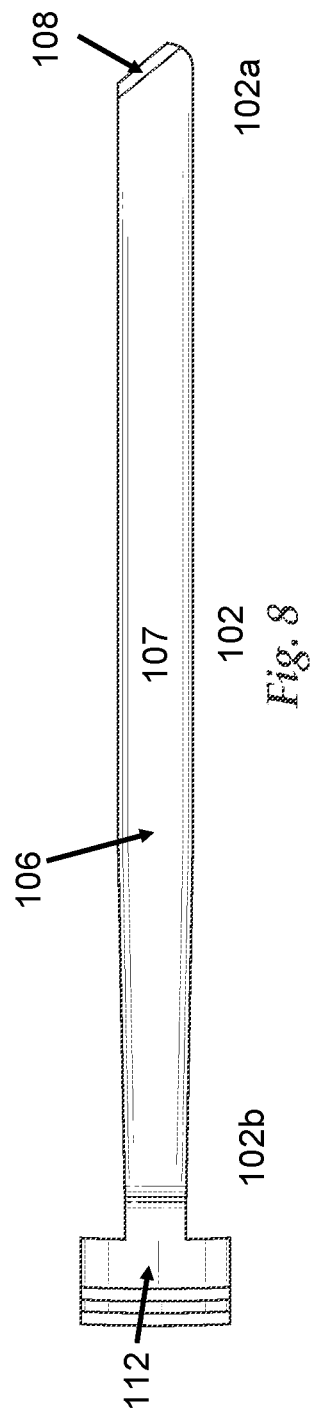

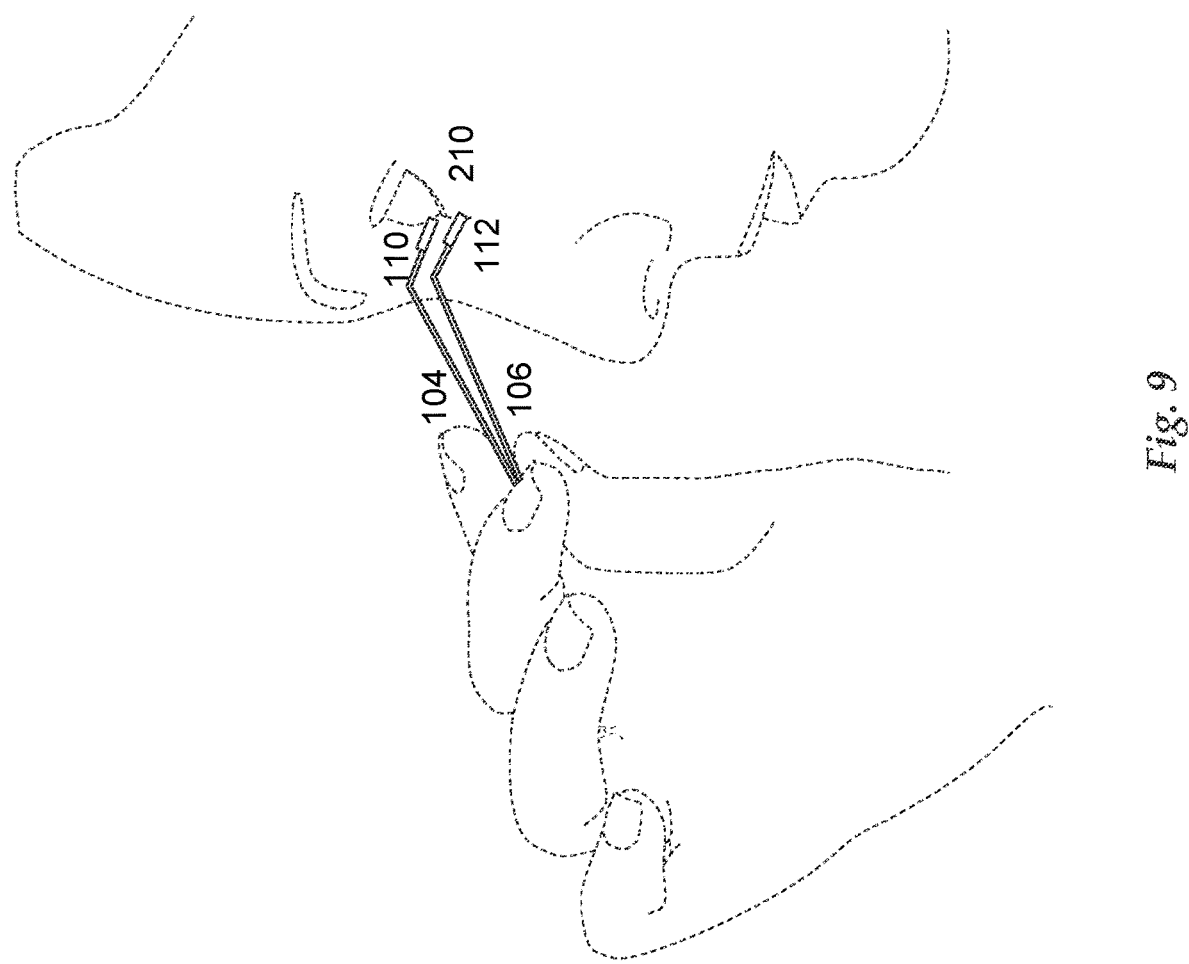

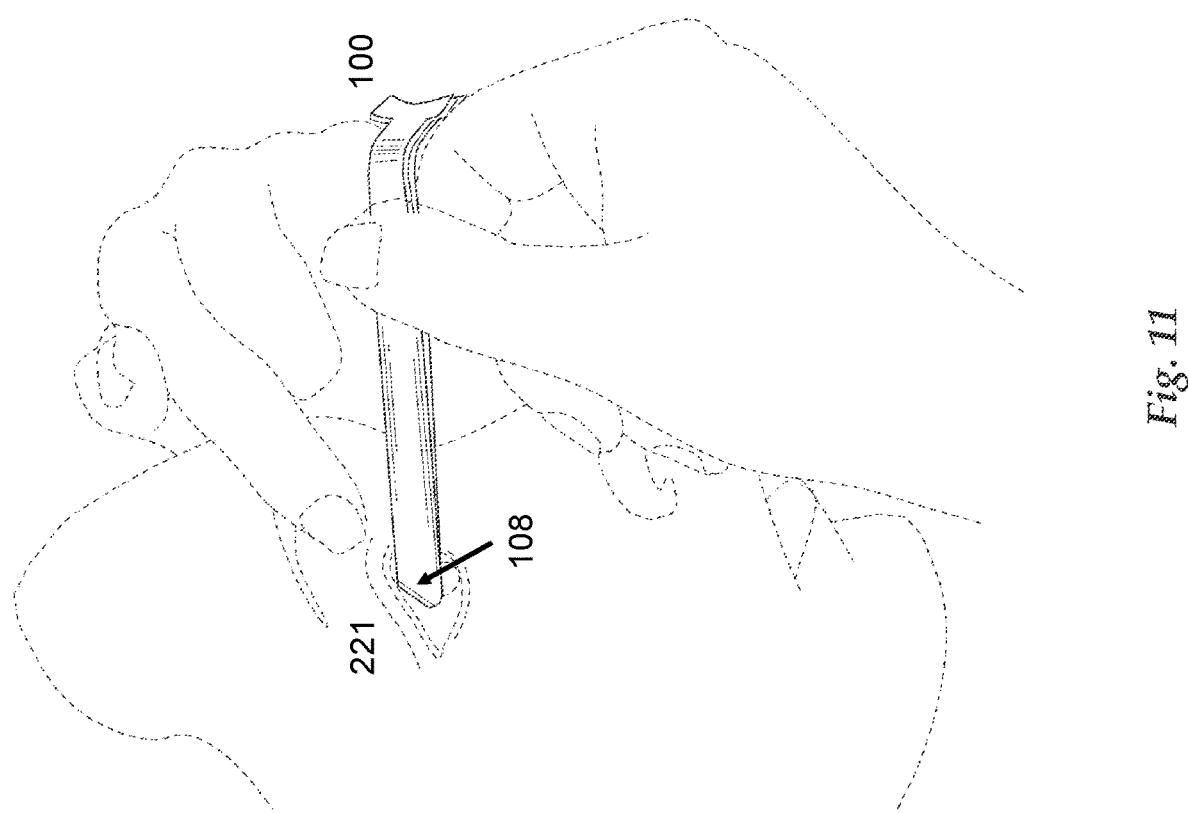

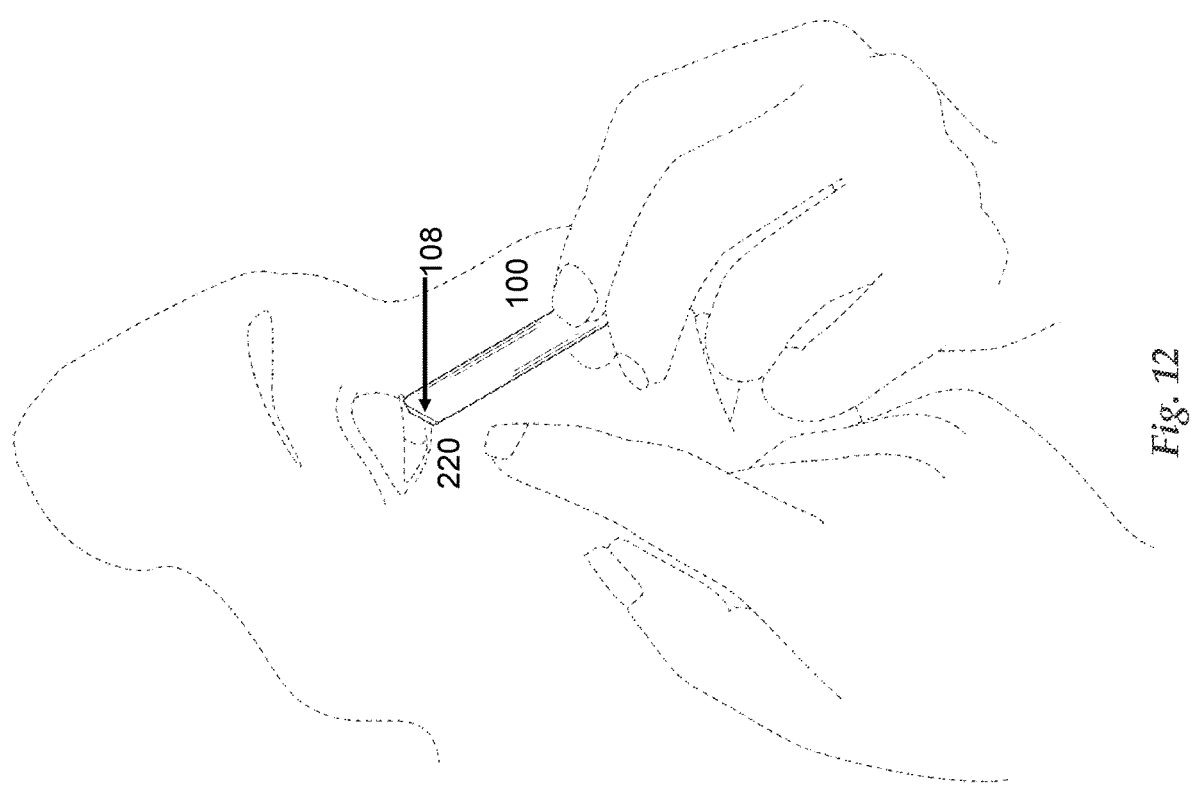

Step 510: Holding the first arm and the second arm of the specialty instrument

→

Step 520: Approaching the eyelid with MGD at a 90° angle to the eyelid margin

→

Step 530: Positioning the first pressure plate 110 on the inside of the eyelid and the second pressure plate 112 in apposition on the outside of the eyelid

→

Step 540: Applying pressure to one or more meibomian glands, and mechanically expressing the one or more meibomian glands via the first pressure plate and the second pressure plate by squeezing the first arm and the second arm towards each other such that the first pressure plate exerts a downward pressure against the eyelid from the inside and the second pressure plate exerts an upward pressure against the eyelid from the outside

*Fig. 13*

OPHTHALMIC SPECIALTY INSTRUMENT FOR TREATING MEIBOMIAN GLAND DYSFUNCTION (MGD)

CROSS REFERENCE TO RELATED APPLICATION

This application claims the benefit and takes priority from U.S. provisional patent application No. 63/307,406 filed on Feb. 7, 2022, the contents of which are herein incorporated by reference.

BACKGROUND OF THE INVENTION

Field of the Invention

This disclosure relates generally to an apparatus and an associated method of use for treating dry eye syndrome and other related conditions. More particularly, the present disclosure relates to a self-treating ophthalmic specialty instrument preferably configured for the treatment of Meibomian Gland Dysfunction (MGD) via lid exfoliation and forced expression.

Description of the Related Art

Meibomian Gland Dysfunction (MGD) is the leading cause of dry eye disease, which is a chronic condition affecting 86% of dry eye disease. It is a common eye condition where the meibomian glands are clogged or when they are not secreting enough oil to maintain a lubricious optical surface. Symptoms of MGD include burning, itching, light sensitivity, and dryness, and may lead to eyelid inflammation and visual symptoms.

Meibomian glands (also called tarsal glands, palpebral glands, and transconjunctival glands) are sebaceous glands along the rims of the eyelid inside the tarsal plate. These glands discharge oil which forms one of the three layers—oil, water, and mucus—of the tear film that lubricates and prevent water from prematurely evaporating, which keeps the eyes moist. However, if the meibomian glands are clogged, the water layer may become dry as water evaporates more quickly in the absence of a sufficient oil layer.

Many instruments are designed to help patients with dry eye conditions to express oil which protects the aqueous element of tears from premature evaporation through the open orifices of the meibomian glands.

Some prior art instruments including forceps are configured to allow doctors to approach a patient's eyelid tangentially and express the clogged meibomian glands which is not ideal if the patient operates the instrument without any physician supervision as the expression is not optimized.

Some prior art instruments disclose forceps with bent tips but the tips are angled along a longitudinal axis of the forceps which makes it infeasible to use the forceps to approach a patient's eyelid perpendicularly.

Other prior art instruments fail to include a debride or exfoliating component which makes it more cumbersome and renders the treatment less effective.

SUMMARY OF THE INVENTION

The instant device and accompanying method of use, as illustrated herein, is clearly not anticipated, rendered obvious, or even present in any of the prior art mechanisms, either alone or in any combination thereof. Thus, the several embodiments of the instant device and method are illustrated herein.

A primary object of the instant disclosure is a new ophthalmic specialty instrument and method configured to help patients with Meibomian Gland Dysfunction (MGD) to self-treat without the supervision of a health care provider by exfoliating the eyelid margin to facilitate the opening of the meibomian gland orifices and expressing the meibum glands via the ophthalmic specialty instrument that is perpendicular to the eyelid.

In one aspect, provided is a new ophthalmic specialty instrument that is easy to operate by a patient with dry eye conditions for the treatment of MGD through lid exfoliation and forced expression, wherein by utilizing the specialty instrument, the patient may approach the eyelid at a substantively right angle as opposed to going sideways at the eyelid to effectively facilitate the clearing of the meibomian glands.

Accordingly, certain aspects are directed to an ophthalmic specialty instrument configured to allow patients to treat MGD and other dry eye conditions by themselves without the need for an ophthalmologist or optometrist, wherein the instrument is easy to operate and more effective. In one embodiment, the ophthalmic specialty instrument comprises a main body having two arms, each arm possessing a distal end and a proximal end; wherein the two arms are pivotably coupled together at a common connection point at the proximal end of each arm, and each arm further includes an angled and slightly wedged pressure plate attached to the distal end; wherein an exfoliating member is attached to the proximal end of each arm at the common connection point; and wherein each pressure plate is angled downwardly and outwardly from a longitudinal plane of each corresponding arm and possessing a gentle radius of curvature to substantially match the curvature of a patient's eyelid thereby facilitating a ninety degree approaching angle to the eyelid margin as opposed to making contact with the eyelids tangentially.

In one embodiment, each pressure plate possesses a gentle radius of curvature of twelve millimeters to accommodate a wide range of contour of a patient's eyelid margin such that the curvatures of the pressure plates match the curvature of the eyelid. In alternative embodiments, the radius of the curvature of each pressure plate may vary depending on a patient's particular need and use for the instrument. Additionally, the pressure plates possess both a distal end and proximal end, wherein the distal end of each pressure plate possesses a greater thickness than the proximal end as the thickness gradually decreases from the distal end to the proximal end. The alignment in turn generates a slight wedging effect to enable a patient to express a proportional and directional pressure gradient from the distal end to the proximal end of the pressure plate to generate more effective secretions to unblock the meibum gland openings from the eyelids. In one preferred embodiment, each pressure plate is thicker at the distal end preferably with a width of one millimeter and tapers up to approximately eight tenths of a millimeter at the proximal end that is connected to each arm of the ophthalmic specialty instrument.

In one embodiment, the pressure plates have non-curved flat surfaces, wherein the distal ends are defined by non-marring round edges to minimize the risk of damaging the delicate skins in the proximity of eyelids and eyeballs.

In one embodiment, the ophthalmic specialty instrument has dual-function which allows a patient to initially clear the meibomian gland orifices of debris and open them using the exfoliating member and then express the clogged glands using the pressure plates.

In another embodiment, the arms preferably made from a material selected from the group consisting of: an alloy blend of steel, chromium, nickel, and cobalt, which is non-magnetic and non-corrosive and may resist temperatures up to 1000° F. Alternatively, the arms are made of materials selected from the group consisting of high tensile strength chromium/carbon steel alloy, non-magnetic stainless steel, titanium, carbon steel, stainless steel alloy, and plastic composites.

In one embodiment, the pressure plates are preferably made of medical-grade plastic composites to allow the instrument to be disposed after a single use which are configured to be removably attached to the distal end of the two arms.

In other embodiments, the pressure plates are made of metal composites, ceramics, or polymers as they are fully reusable or partially reusable.

In one embodiment, the pressure plates are angled between thirty degrees to eighty degrees downwardly and outwardly from the longitudinal planes of the arms.

In another embodiment, the pressure plates are angled to preferably forty-five degrees to accommodate the approaching angle more effectively when the instrument is operated by a patient without the supervision of a health care provider.

In one embodiment, the pressure plates are rectangles, squares, or circles, and they are configured to be substantially parallel to each other such that directional expressions to the meibomian glands are optimized.

In yet another embodiment, the surface of the pressure plates is coated with a long lasting PVC or rubber coated with other similar material which is non-scratching and non-marring.

In one embodiment, the gap between the first pressure plate and the second pressure plate is about 6 mm.

In one embodiment, the exfoliating member is 25 mm long and is gently curved to exfoliate keratinized cells and debride the lid margin to facilitate the opening of the clogged meibomian gland orifices.

In one embodiment, the exfoliating member is recessed into the proximal end and extends longitudinally such that a back end of the exfoliating member is flush with the common connection point of the two arms.

There has thus been outlined, rather broadly, the more important features of the ophthalmic specialty instrument, in order that the detailed description thereof that follows may be better understood, and in order that the present contribution to the art may be better appreciated. There are additional features of the system that will be described hereinafter and which will form the subject matter of the claims appended hereto.

In this respect, before explaining at least one embodiment of the system in detail, it is to be understood that the instrument and accompanying method is not limited in its application to the details of construction and to the arrangements of the components set forth in the following description, and/or illustrated in the drawings. The instrument is capable of other embodiments and of being practiced and carried out in various ways. Also, it is to be understood that the phraseology and terminology employed herein are for the purpose of description and should not be regarded as limiting.

These together with other objects of the instrument, along with the various features of novelty, which characterize the instrument and method of use, are pointed out with particularity in the claims annexed to and forming a part of this disclosure. For a better understanding of the instrument, its operating advantages and the specific objects attained by its uses, reference should be made to the accompanying drawings and descriptive matter in which there are illustrated preferred embodiments of the system.

The foregoing has outlined the more pertinent and important features of the instrument and method of use in order that the detailed description of the system that follows may be better understood, and the present contributions to the art may be more fully appreciated. It is of course not possible to describe every conceivable combination of components and/or methodologies, but one of ordinary skill in the art may recognize that many further combinations or permutations are possible. Accordingly, the novel architecture described below is intended to embrace all such alterations, modifications, and variations that fall within the spirit and scope of the appended claims.

BRIEF DESCRIPTION OF THE DRAWINGS

FIG. 1 illustrates a schematic diagram showing a perspective view of the ophthalmic specialty instrument for treating MGD.

FIG. 2 illustrates a schematic diagram showing another perspective view of the ophthalmic specialty instrument for treating MGD.

FIG. 3A illustrates a schematic diagram showing the front of the pressure plates of the ophthalmic specialty instrument for treating MGD.

FIG. 3B illustrates a schematic diagram showing the front of the pressure plates of the ophthalmic specialty instrument for treating MGD with non-marring edges.

FIG. 4 illustrates a schematic diagram showing the back of the ophthalmic specialty instrument for treating MGD.

FIG. 5 illustrates a schematic diagram showing the left side of the ophthalmic specialty instrument for treating MGD.

FIG. 6 illustrates a schematic diagram showing the right side of the ophthalmic specialty instrument for treating MGD.

FIG. 7 illustrates a schematic diagram showing the top of the ophthalmic specialty instrument for treating MGD.

FIG. 8 illustrates a schematic diagram showing the bottom of the ophthalmic specialty instrument for treating MGD.

FIG. 9 illustrates a schematic diagram showing a user using the ophthalmic specialty instrument to treat the lower eyelid.

FIG. 11 illustrates a schematic diagram showing a user using the exfoliator member of the ophthalmic specialty instrument to debride the upper eyelid margin.

FIG. 12 illustrates a schematic diagram showing a user using the exfoliator member of the ophthalmic specialty instrument to debride the lower eyelid margin.

FIG. 13 illustrates a flow chart showing a method of treating MGD.

DETAILED DESCRIPTION OF THE SEVERAL EMBODIMENTS

Figure 10:
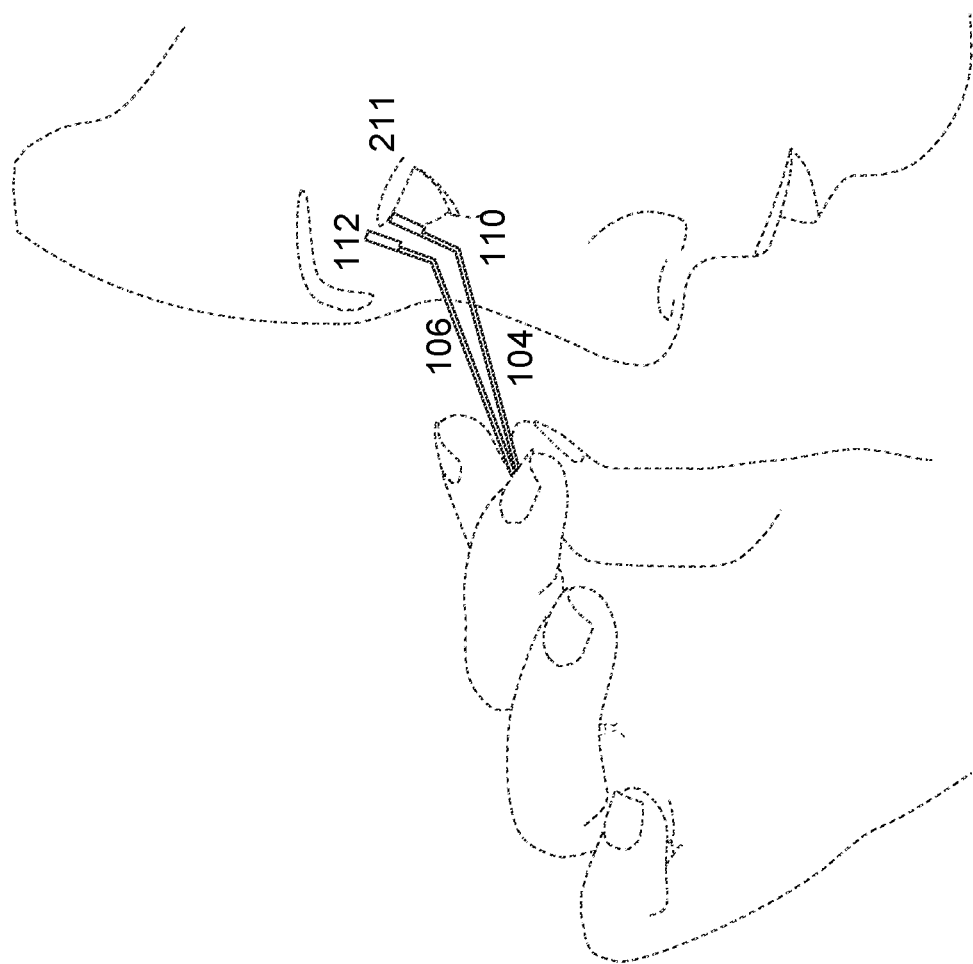
FIG. 10 illustrates a schematic diagram showing a user using the ophthalmic specialty instrument to treat the upper eyelid.

Reference will now be made to non-limiting embodiments, examples of which are illustrated in the Figures. FIGS. 1-2 illustrate a pair of two perspective views of an ophthalmic specialty instrument for treating MGD. In a preferred embodiment, the ophthalmic specialty instrument 100 comprises a main body 102 with a proximal end 102a and a distal end 102b, wherein the main body 102 further comprises a first arm 104 with a substantially flat surface on a first longitudinal plane 105 coupled to a second arm 106 with a substantially flat surface on a second longitudinal plane 107. The first arm 104 is configured to be stacked over the second arm 106 such that the first longitudinal plane 105 and the second longitudinal plane 107 are extended from a common pivotal connecting point 109 located near the proximal end 102a of the main body 102. In some embodiments, the arms 104 and 106 are made from an alloy blend of steel, chromium, nickel, and cobalt, which is non-magnetic and non-corrosive and may resist temperatures up to 1000° F. Alternatively, the first and second arms 104, 106 may be made of materials selected from the group consisting of high tensile strength chromium/carbon steel alloy, non-magnetic stainless steel, titanium, carbon steel, stainless steel alloy, and plastic composites. In one embodiment, the proximal end 102a of the instrument 100 is defined by a gently curved edge.

To facilitate the positioning of the specialty instrument 100 at the distal end 102b, the first arm 104 and the second arm 106 are bent downwardly and outwardly at an angle 120, preferably at forty-five degrees, from the first longitudinal plane 105 and the second longitudinal plane 107 respectively, wherein the first arm 104 is fixedly attached to a first pressure plate 110 and the second arm 106 is fixedly attached to a second pressure plate 112.

Each arm 104, 106 is configured to form the obtuse angle 120 with its respective pressure plate. The angle 120, as shown in FIG. 5, may range from thirty degrees to eighty degrees, and preferably at forty-five degrees to accommodate the approaching angle more effectively when the instrument 100 is operated by a patient without the supervision of a health care provider. The pressure plates 110 and 112 may have various shapes, including a rectangle, a square, a circle, etc., and they are configured to be substantially parallel to each other such that directional expressions to the meibomian glands are optimized. In some embodiments, the pressure plates 110 and 112 are coated with long lasting PVC or rubber coated with other similar material which is non-scratching and non-marring. In yet another embodiment, a gap 150 between the first pressure plate 110 and the second pressure plate 112 is approximately six to eight millimeters. In one embodiment, the pressure plates 110, 112 are removably attached to the distal ends 102b of the elongated arms 104, 106.

In a preferred embodiment, the proximal end 102a of the main body 102 comprises an exfoliating member 108 that may be around twenty-five millimeters in length with a peripheral edge 108a designed to exfoliate keratinized cells (hardened cells filled with protein) and debride the lid margin to facilitate the opening of the clogged meibomian gland orifices before pressure can be mechanically applied on the glands directly using the pressure plates 110 and 112 based on the severity of the condition. Both the first pressure plate 110 and the second pressure plate 112 have mild concave curvatures of approximately twelve millimeters downwardly to accommodate a wide range of contour of a patient's eyelid margin such that the curvatures of the pressure plates match the curvature of the eyelid which allows for complete contact to the eyelids and reduce the risk of unnecessary pulling and other types of damages. In alternative embodiments, the radius of the curvature of each pressure plate 110, 112 may vary depending on a patient's particular need and use for the instrument.

Additionally, the first and second pressure plates 110 and 112 comprise distal ends 110a and 112a and proximal ends 110b and 112b respectively, wherein the distal ends 110a and 112a are wider than the corresponding proximal ends 110b and 112b, thereby creating a slight wedging effect to enable a user to express a proportional and directional pressure gradient from the distal ends 110a, 110b to the proximal ends 112a, 112b of the pressure plates 110, 112 so as to generate more effective secretions to unblock the meibum gland openings from the eyelids.

In some embodiments, the distal ends 110a, 112a of each pressure plate 110, 112 are one millimeter in width and the proximal ends 110b, 112b of each pressure plate 110, 112 are eight tenths of one millimeter. The tapering of the pressure plates 110, 112 is designed to allow for more directional pressure on a patient's eyelid.

Further, in one embodiment, the exfoliating member 108 and the pressure plates 110 and 112 are removably attached to the main body 102. Further, the exfoliating member 108 is recessed into the proximal end 102a of the main body 102.

FIG. 3a illustrates the front view of the preferred embodiment of the specialty instrument, namely, the slightly curved pressure plates 110 and 112, wherein both pressure plates 110, 112 are angled downwards from the first and the second longitudinal planes 105, 107 of the elongated arms 104, 106. In the preferred embodiment, the pressure plates 110 and 112 are configured with a radius of curvature of about 0.12 mm.

In another embodiment as illustrated in FIG. 3b, the pressure plates 130, 132 are flat and non-curved, wherein the distal ends 130a, 132a are defined by non-marring round edges 130c, 132c to minimize the risk of damaging the delicate skins in the proximity of eyelids and eyeballs.

FIG. 4 illustrates the back view of the preferred embodiment of the specialty instrument, including the exfoliating member 108 located near the proximal end 102a, the first arm 104 with the first pressure plate 110, the second arm 106 with the second pressure plate 112, wherein the first pressure plate 110 further comprises the distal end 110a and the proximal end 110b, and wherein the second pressure plate 112 further comprises the distal end 112a and the proximal end 112b. In some embodiments, the first and the second pressure plates are made of medical-grade plastic composites as they are disposable after a single use which are configured to be removably attached to the arms 104 and 106 at the distal end 102b. In other embodiments, the pressure plates are made of metal composites, ceramics, or polymers as they are fully reusable or partially reusable.

FIGS. 5 and 6 illustrate the left and right-side views of the angled distal end 102b with the curved pressure plates 110 and 112 in the preferred embodiment. The overall length and width of the specialty instrument 100 may vary. However, in some embodiments, the length is between eighty to one hundred and twenty millimeters; the width is between five and ten millimeters; the length of the angled portion including the pressure plates is between ten and fifteen millimeters; and the average thickness of the specialty instrument is about six millimeters. The first arm 104 and the second arm 106 of the main body 102 preferably comprise continuous flat surfaces between the distal end 102a and the proximal end 102b.

The top and the bottom views of the specialty instrument 100 are shown in FIGS. 7 and 8. In one preferred embodiment, the width of the distal end 102b of the main body 102 is slightly smaller than that of the proximal end 102a. The overall thickness and the width of the exfoliating member 108 does not exceed those of the main body 102. In other embodiments, the overall width of the arms 104 and 106 are substantially the same.

FIG. 9 illustrates a schematic diagram showing a user using the ophthalmic specialty instrument 100 to treat a lower eyelid 210 of the user by positioning the instrument 100 at a 90° angle as it approaches the lower eyelid 210. The first pressure plate 110 is placed against the palpebral conjunctiva inside the lower eyelid 210 and the second pressure plate 112 is placed outside the lower eyelid 210 such that the user may exert pressure on the lower eyelid 210 by squeezing the first arm 104 and the second arm 106 against each other.

FIG. 10 illustrates a schematic diagram showing a user using the ophthalmic specialty instrument 100 to treat the upper eyelid 211 of the user by positioning the instrument at a 90° angle as it approaches the upper eyelid 211. The first pressure plate 110 is placed against the palpebral conjunctiva inside the upper eyelid 211 and the second pressure plate 112 is placed outside the upper eyelid 211 such that the user may exert pressure on the upper eyelid 211 by squeezing the first arm 104 and the second arm 106 against each other.

FIGS. 11-12 illustrate schematic diagrams showing a user utilizing the exfoliator member 108 of the ophthalmic specialty instrument 100 to debride his or her upper eyelid margin 221 and the lower eyelid margin 220. In one embodiment, the exfoliating member 108 is 25 mm long and is gently curved to exfoliate keratinized cells and debride the eyelid margins to facilitate the opening of the clogged meibomian gland orifices before pressuring the glands directly using the pressure plates based on the severity of the condition. In another embodiment, the exfoliating member 108 is recessed into the proximal end of the instrument 100 and extended longitudinally such that the back end of the exfoliating member is flush with the common pivotal connecting point.

Figure 14:
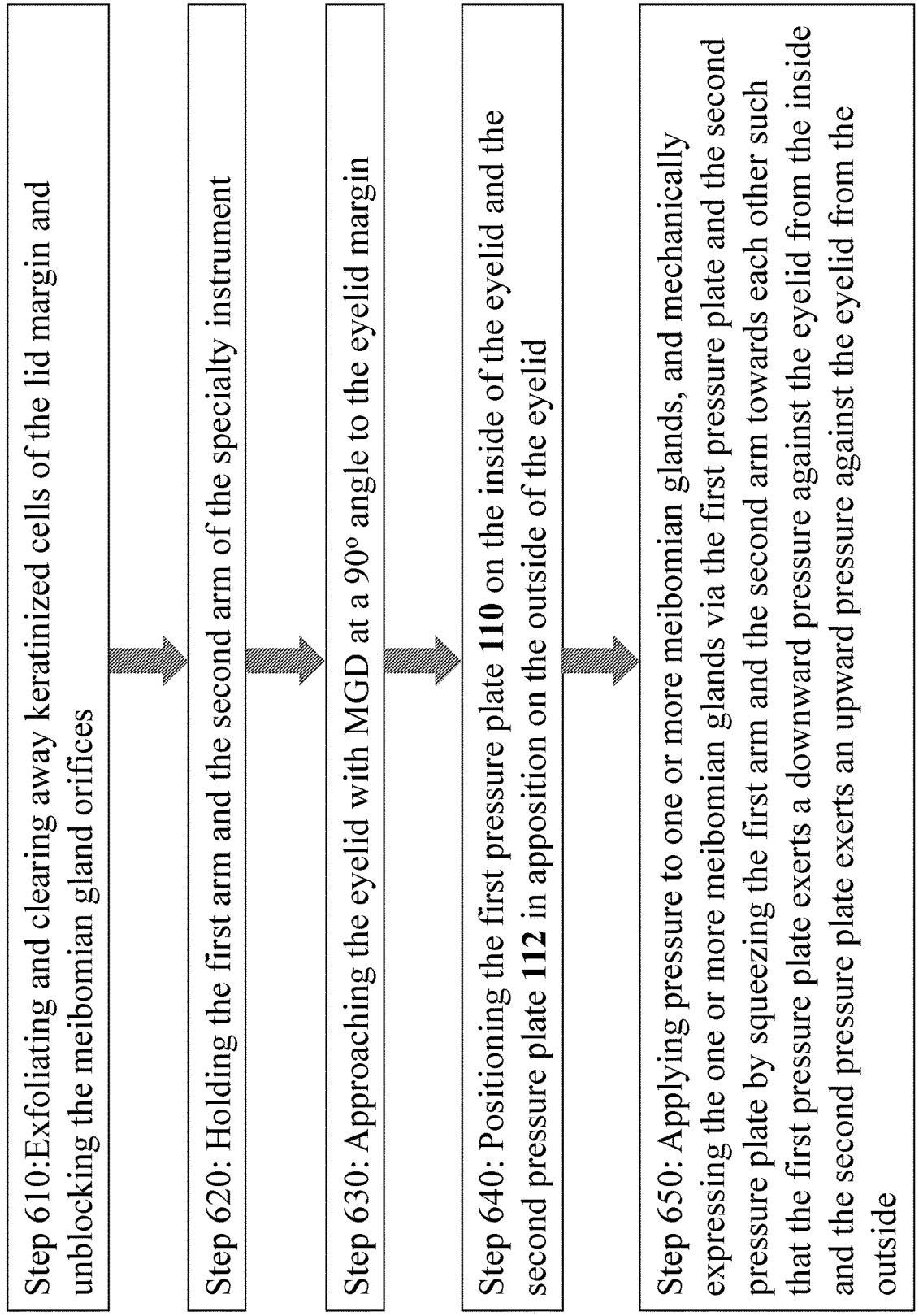
FIG. 14 illustrates another flow chart showing another method of treating MGD with an exfoliating member attached to the main body of the ophthalmic specialty instrument.

FIG. 13 illustrates a flow diagram for one method of treating patients with MGD 3, wherein initially at step 510, a patient is holding the first and the second arms of the specialty instrument near the middle of the main body. At step 520, the patient is approaching the eyelid with MGD syndrome at a substantially ninety-degree angle (preferably between eighty-five to ninety-five degrees to the eyelid margin (as opposed to sideways as taught in the relevant art)). At step 530, the patient is positioning the first pressure plate 110 on the inside of the eyelid and the second pressure plate 112 in apposition on the outside of the eyelid. At step 540, the patient is applying pressure to one or more meibomian glands and mechanically expressing the one or more meibomian glands via the first pressure plate 110 and the second pressure plate 112 by squeezing the first arm and the second arm towards each other such that the first pressure plate exerts a downward pressure against the eyelid from the inside and the second pressure plate exerts an upward pressure against the eyelid from the outside. Alternatively, In another method of treating patients with more severe MGD as shown in FIG. 14, if the one or more meibomian glands are severely clogged, the patient may first use the exfoliating member to unclog the meibomian glands gently before positioning the pressure plates on the distal end of the specialty instrument over the eyelid. At step 610, the patient is exfoliating the clearing away keratinized cells (hardened cells filled with protein) of the lid margin to unblock the meibomian gland orifices of debris and dead cells, which allows for easier expression of meibomian gland content. At step 620, the patient is holding the first arm and the second arm of the specialty instrument near the middle portion of the main body. At step 630, the patient is approaching the eyelid with MGD at a substantially 90° angle (preferably between eighty-five to ninety-five degrees to the eyelid margin to the eyelid margin). At step 640, the patient is positioning the first pressure plate on the inside of the eyelid and the second pressure plate in apposition on the outside of the eyelid. At step 650, the patient is applying pressure to one or more meibomian glands and mechanically expressing the one or more meibomian glands via the first and the second pressure plates by squeezing the first and the second arms toward each other such that the first pressure plate exerts a downward pressure against the eyelid from the inside and the second pressure plate exerts an upward pressure against the eyelid from the outside.

As shown herein, an ophthalmic specialty instrument configured to allow patients to treat MGD and other dry eye conditions themselves which is easy to operate and more effective is disclosed by utilizing a pair of angled and slightly wedged pressure plates attached to the distal ends of two arms and an exfoliating member attached to the proximal end of the arms; wherein the two arms are pivotably coupled to a common connection point; and wherein the pressure plates are bent downwardly and outwardly from the longitudinal planes of the arms and have gentle radius of curvature that match the curvature of eyelids.

What is claimed is:

1. An ophthalmic specialty instrument configured for treating meibomian gland dysfunction, the instrument comprising:
    a main body having a distal end and a proximal end, wherein the main body further comprises:
        a first elongated arm having a first longitudinal plane; and
        a second elongated arm having a second longitudinal plane;
    wherein the first elongated arm and the second elongated arm are stacked in a vertical direction such that the first longitudinal plane and the second longitudinal plane are connected and extended from a common pivotal connection point at the proximal end of the main body; and
    wherein the first elongated arm and the second elongated arm are bent downwardly and outwardly from the first longitudinal plane and the second longitudinal plane respectively to form a first angle and a second angle at the distal end of the main body and comprise continuous flat surfaces between the distal and the proximal end;
    a first pressure plate attached to the first elongated arm at the distal end of the main body;
    a second pressure plate attached to the second elongated arm at the distal end of the main body;
    wherein the first pressure plate and the second pressure plate possess concave curvatures; and
    wherein a thickness of the first pressure plate and the second pressure plate decreases from a distal end of each pressure plate to a proximal end of each pressure plate.

2. The ophthalmic specialty instrument of claim 1, wherein the main body further comprises an exfoliator located at the proximal end of the main body.

3. The ophthalmic specialty instrument of claim 2, wherein a back end of the exfoliator is recessed into the proximal end of the main body.

4. The ophthalmic specialty instrument of claim 1, wherein a thickness and a width of the exfoliator do not exceed a thickness and a width of the main body.

5. The ophthalmic specialty instrument of claim 1, wherein a width of the distal end is smaller than a width of the proximal end of the main body to allow for better gripping position.

6. The ophthalmic specialty instrument of claim 1, wherein the first and the second angles are 45 degrees to accommodate a utilization of the ophthalmic specialty apparatus by a patient without any supervision of a health care professional.

7. The ophthalmic specialty instrument of claim 1, wherein the first and the second angles are between 30 degrees and 80 degrees.

8. The ophthalmic specialty instrument of claim 1, wherein the distal ends of the first and the second pressure plates are 1 mm in width; and
wherein the proximal ends of the first and the second pressure plates are 0.8 mm in width.

9. The ophthalmic specialty instrument of claim 1, wherein a radius of the concave curvatures of the first and the second pressure plates is 0.12 mm.

10. The ophthalmic specialty instrument of claim 1, wherein the pressure plates are removably attached to the distal end of the main body.

11. The ophthalmic specialty instrument of claim 1, wherein the distal ends of the first and the second pressure plates comprise non-marring round edges.

12. The ophthalmic specialty instrument of claim 1, wherein the first and the second elongated arms are made of an alloy that are non-magnetic, non-corrosive, and heat-resistant with materials selected from the group consisting of high tensile strength steel, chromium, nickel, cobalt, carbon steel alloy, non-magnetic stainless steel, titanium, carbon steel, stainless steel alloy, and plastic composites.

13. The ophthalmic specialty instrument of claim 1, wherein the first and the second pressure plates are made of material selected from the group consisting of medical-grade plastic composites, ceramics, polymers, and metal composites.

14. The ophthalmic specialty instrument of claim 1, wherein a coated surface of the first and the second pressure plates is non-scratching and non-marring.

15. The ophthalmic specialty instrument of claim 1, wherein a gap between the first pressure plate and the second pressure plate is 6 mm.

16. A method for treating meibomian gland dysfunction utilizing the ophthalmic specialty instrument of claim 1, the method comprising the steps of:
holding a first elongated arm and a second elongated arm of an ophthalmic specialty instrument by a proximal end of the ophthalmic specialty apparatus;
approaching an eyelid margin of a patient with the ophthalmic specialty instrument at a substantially 90-degree angle to the eyelid margin;
positioning a first pressure plate attached to a distal end of the first elongated arm on an inside of the eyelid margin and a second pressure plate attached to a distal end of the second elongated arm on an outside of the eyelid margin; and
applying pressure to one or more meibomian glands and mechanically expressing the one or more meibomian glands via the first pressure plate and the second pressure plate by squeezing the first elongated arm and the second elongated arm.

17. A method for treating meibomian gland dysfunction, utilizing the ophthalmic specialty instrument of claim 1, the method comprising the steps of:
unblocking meibomian gland orifices of an eyelid margin by exfoliating and clearing away keratinized cells of the eyelid margin using an exfoliator located on a distal end of an ophthalmic specialty instrument;
holding a first elongated arm and a second elongated arm of an ophthalmic specialty instrument by a proximal end of the ophthalmic specialty apparatus;
approaching an eyelid margin of a patient with the ophthalmic specialty instrument at a substantially 90-degree angle to the eyelid margin;
positioning a first pressure plate attached to a distal end of the first elongated arm on an inside of the eyelid margin and a second pressure plate attached to a distal end of the second elongated arm on an outside of the eyelid margin; and
applying pressure to one or more meibomian glands and mechanically expressing the one or more meibomian glands via the first pressure plate and the second pressure plate by squeezing the first elongated arm and the second elongated arm.

\* \* \* \* \*